United States Patent
Zhang

(10) Patent No.: US 10,143,438 B2
(45) Date of Patent: Dec. 4, 2018

(54) SYSTEM FOR 3D OBJECT MODELING AND TRACKING IN X-RAY IMAGING

(71) Applicant: Xiang Zhang, Vienna, VA (US)

(72) Inventor: Xiang Zhang, Vienna, VA (US)

( * ) Notice: Subject to any disclaimer, the term of this patent is extended or adjusted under 35 U.S.C. 154(b) by 229 days.

(21) Appl. No.: 15/220,585

(22) Filed: Jul. 27, 2016

(65) Prior Publication Data

US 2017/0035382 A1 Feb. 9, 2017

Related U.S. Application Data

(60) Provisional application No. 62/202,037, filed on Aug. 6, 2015.

(51) Int. Cl.
| | | |
|---|---|---|
| A61B 6/00 | (2006.01) | |
| A61B 90/00 | (2016.01) | |
| A61B 6/12 | (2006.01) | |
| A61B 6/04 | (2006.01) | |

(52) U.S. Cl.
CPC ............... *A61B 6/547* (2013.01); *A61B 6/12* (2013.01); *A61B 6/4441* (2013.01); *A61B 90/39* (2016.02); *A61B 6/0492* (2013.01); *A61B 6/4014* (2013.01); *A61B 6/487* (2013.01); *A61B 2090/3966* (2016.02)

(58) Field of Classification Search
CPC . A61B 2090/3966; A61B 6/0492; A61B 6/12; A61B 6/4014; A61B 6/4441; A61B 6/487; A61B 6/547; A61B 90/39
See application file for complete search history.

(56) References Cited

U.S. PATENT DOCUMENTS

| | | |
|---|---|---|
| 5,732,122 A | 3/1998 | Tibbals |
| 5,772,594 A | 6/1998 | Barrick |
| 6,160,870 A | 12/2000 | Jacobson |
| 6,714,629 B2 | 3/2004 | Vilsmeier |
| 6,856,827 B2 | 2/2005 | Seeley et al. |
| 7,241,045 B2 | 7/2007 | Skalli et al. |
| 7,558,368 B2 | 7/2009 | Klingenbeck-Regn |
| 7,826,884 B2 | 11/2010 | Baumgart |
| 8,104,958 B2 | 1/2012 | Weiser et al. |
| 8,180,130 B2 | 5/2012 | Sebok |
| 8,364,242 B2 | 1/2013 | Li |
| 8,411,927 B2 | 4/2013 | Chang et al. |
| 8,515,527 B2 | 8/2013 | Vaillant et al. |

(Continued)

OTHER PUBLICATIONS

Z. Zhang. A flexible new technique for camera calibration IEEE Transactions on Pattern Analysis and Machine Intelligence 22(11):1330-1334 2000.

(Continued)

*Primary Examiner* — Mark R Gaworecki

(57) ABSTRACT

Disclosed herein is an X-ray imaging system, comprising: a first X-ray source; an image sensor, spaced apart from the first X-ray source; a table configured to be positioned between the first X-ray source and the image sensor and configured to accommodate a person for imaging in the X-ray imaging system; and a fiducial marker system; wherein the fiducial marker system comprises three markers, centers of the three markers not being collinear; wherein at least one of the three markers is distinct. The X-ray imaging system may be used to model the 3D shape and track the 3D motion of an object (e.g., a surgical instrument) in the person.

18 Claims, 12 Drawing Sheets

(56) References Cited

U.S. PATENT DOCUMENTS

| | | |
|---|---|---|
| 8,538,106 B2 | 9/2013 | Ibarz et al. |
| 8,731,642 B2 | 5/2014 | Zarkh et al. |
| 8,768,437 B2 | 7/2014 | Barrick |
| 9,014,423 B2 | 4/2015 | Wang et al. |
| 9,129,427 B2 | 9/2015 | Golubovic et al. |
| 9,142,018 B2 | 9/2015 | Robert et al. |
| 9,149,656 B2 | 10/2015 | Tanabe |
| 9,189,848 B2 | 11/2015 | Sakaguchi et al. |
| 2001/0034480 A1* | 10/2001 | Rasche ............ A61B 6/12 600/407 |
| 2008/0228065 A1 | 9/2008 | Viswanathan et al. |
| 2008/0285724 A1 | 11/2008 | Dehler |
| 2009/0216111 A1 | 8/2009 | Weese et al. |
| 2011/0188726 A1* | 8/2011 | Nathaniel ........... G01N 23/04 382/132 |
| 2015/0297151 A1 | 10/2015 | Florent |
| 2015/0368797 A1 | 12/2015 | LaVoie et al. |
| 2015/0369757 A1 | 12/2015 | Golubovic et al. |
| 2016/0058590 A1 | 3/2016 | Mukai |

OTHER PUBLICATIONS

R.M. Haralick. Review and Analysis of Solutions of the Three Point Perspective Pose Estimation Problem International Journal of Computer Vision 13(3) 331-356 1994.

A. Graves M. Liwicki S. Fernandez R. Bertolami H. Bunke and J. Schmiduber. A novel connectionist system for improved unconstrained handwriting recognition. IEEE Transactions on Pattern Analysis and Machine Intelligence 31 (5) 2009.

R. M. Haralick C. Lee K. Ofienberg and M. Nolle. Analysis and solutions of the three point perspective pose estimation problem. In Proc. of the Int. Conf. on Computer Vision and Pattern Recognition pp. 592-598 1991.

R. E. Karlman. A new approach to linear filtering and prediction problems. The Journal of Basic Engineering 82(35) 1960.

X. Zhang. Numerical instability of projection matrix decomposition—a study with AR applications. In Proc.of the IEEE Int. Symposium on Mixed and Augmented Reality 2004.

* cited by examiner

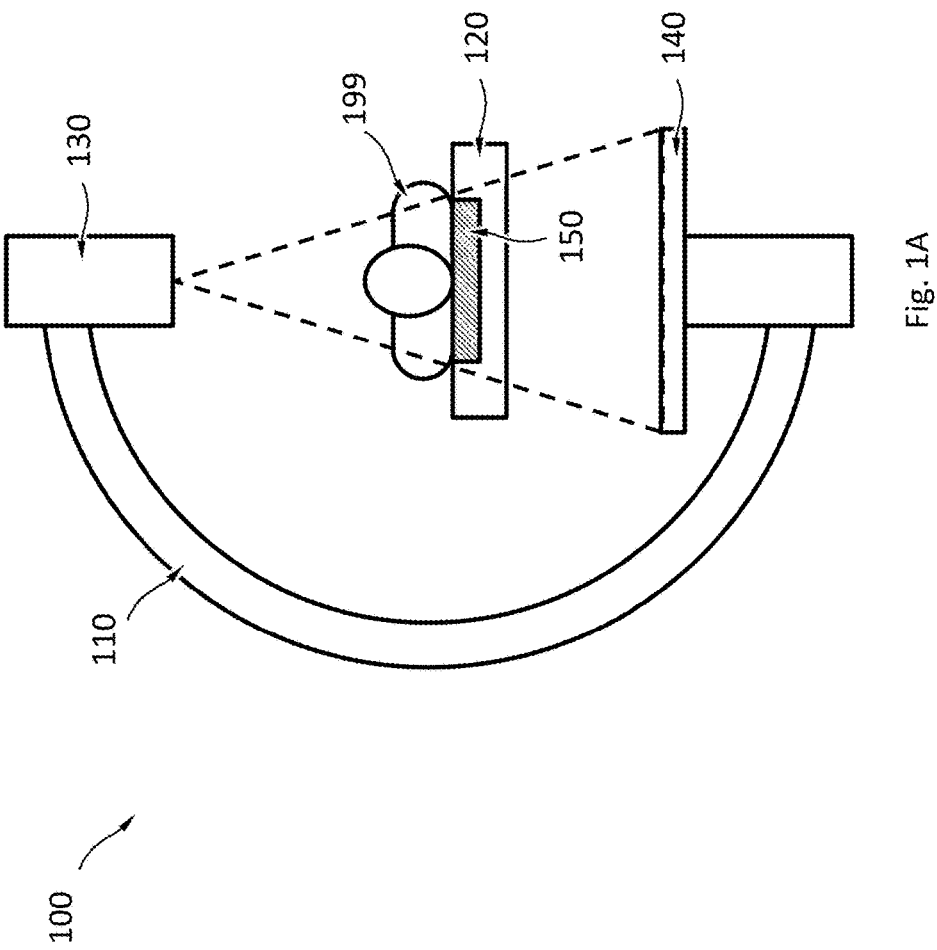

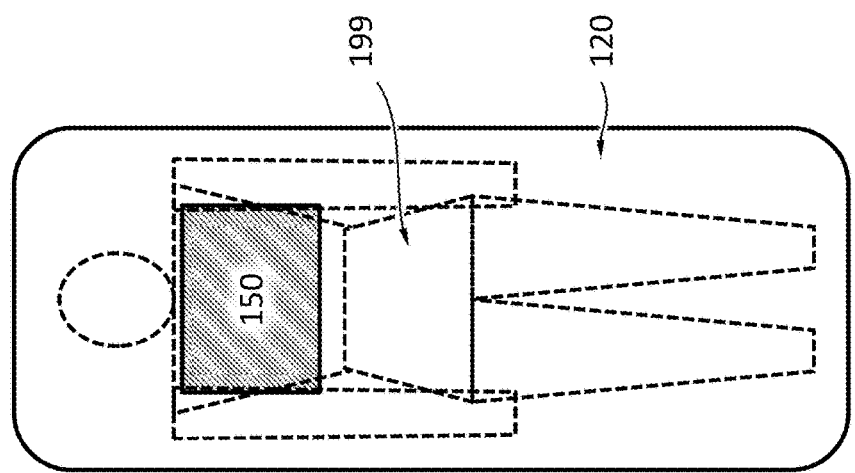

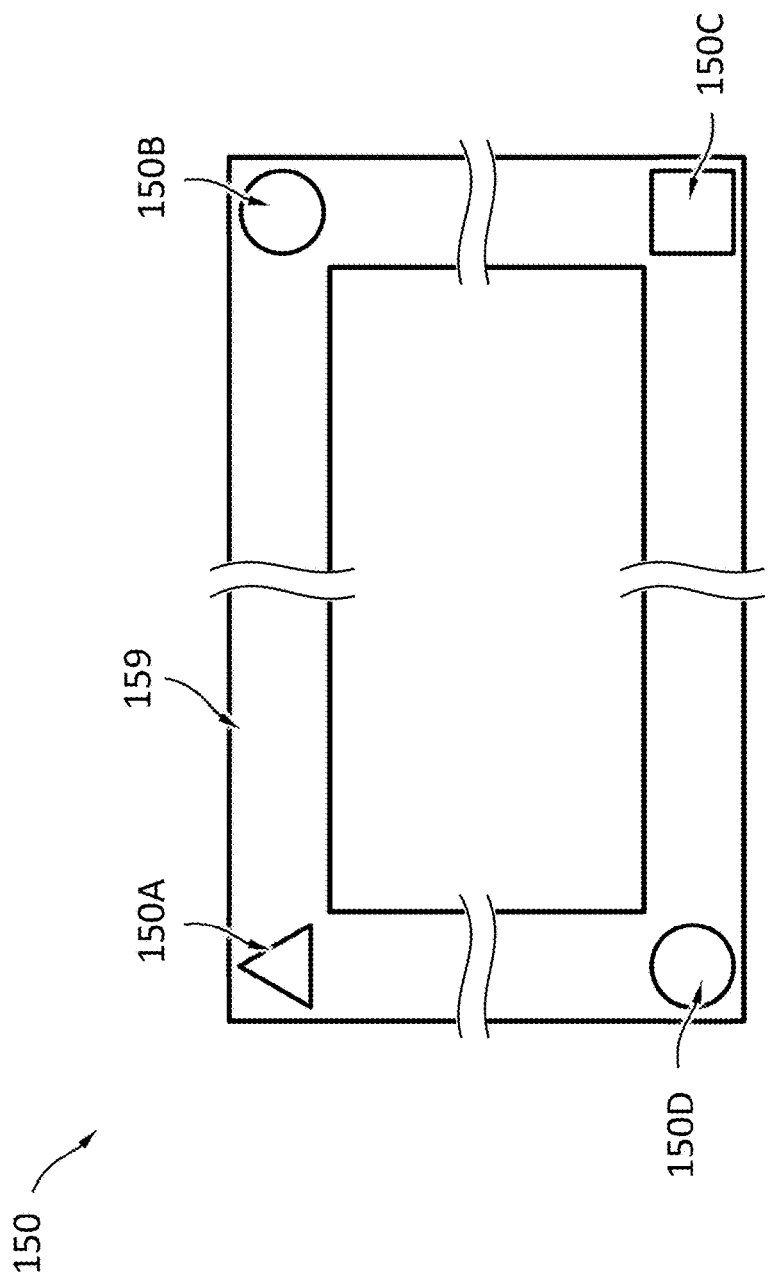

SYSTEM FOR 3D OBJECT MODELING AND TRACKING IN X-RAY IMAGING

CROSS-REFERENCE TO RELATED APPLICATION

This application claims the benefit of U.S. Provisional Patent Application No. 62/202,037 filed on Aug. 6, 2015, the disclosure of which is hereby incorporated by reference in its entirety.

TECHNICAL FIELD

The disclosure herein relates systems and methods of modeling and tracking the motion of an object in X-ray views, such as a surgical apparatus in a human body during surgery.

BACKGROUND

X-ray is a form of electromagnetic radiation that typically has a wavelength ranging from 0.01 to 10 nanometers (corresponding to frequencies in the range of $3\times10^{16}$ Hz to $3\times10^{19}$ Hz and photon energies in the range of 100 eV to 100 keV.

X-ray has been extensively used in imaging for about a century. Due to its penetrating ability, X-ray is useful to obtain images of the inside of subjects, e.g., in medical radiography and airport security. In X-ray imaging, an X-ray source generates X-ray; the X-ray is directed to a subject; the X-ray that is backscattered from or penetrates the subject forms a scene; an image sensor forms an image of the scene. One example of X-ray imaging techniques is fluoroscopy. Fluoroscopy is an imaging technique that uses X-rays to obtain real-time (or nearly real-time) moving images of the interior of a subject. In its primary application of medical imaging, a fluoroscope allows a physician to see the internal structure and function of a patient (e.g., the pumping action of the heart or the motion of swallowing). This is useful for both diagnosis and therapy and occurs in general radiology, interventional radiology, and image-guided surgery. In its simplest form, a fluoroscope consists of an X-ray source and a fluorescent screen, between which a patient is placed. Since the 1950s most fluoroscopes have included X-ray image intensifiers and cameras as well, to improve the image's visibility and make it available on a remote display screen.

Images obtained in X-ray imaging are usually 2D representations of the internal structure of the subject. Although techniques such as X-ray computed tomography (X-ray CT) is available to generate a 3D representation of the subject, these techniques often involve extensive computation from a large number of images, and thus are not suitable for real-time imaging.

SUMMARY

Disclosed herein is an X-ray imaging system, comprising: a first X-ray source; an image sensor, spaced apart from the first X-ray source; a table configured to be positioned between the first X-ray source and the image sensor and configured to accommodate a person for imaging in the X-ray imaging system; and a fiducial marker system; wherein the fiducial marker system comprises three markers, centers of the three markers not being collinear; wherein at least one of the three markers is distinct.

According to an embodiment, the X-ray imaging system further comprises a C-arm, wherein the first X-ray source and the image sensor are mechanically connected by the C-arm.

According to an embodiment, the first X-ray source and the image sensor are movable relative to the table.

According to an embodiment, the fiducial marker system and the table are connected in such a way that the fiducial marker system does not move relative to the table during imaging.

According to an embodiment, the fiducial marker system is an integral portion of the table.

According to an embodiment, the fiducial marker system is configured to be positioned such that at least some part of the fiducial marker system is visible in an image captured by the image sensor during imaging by the X-ray imaging system.

According to an embodiment, the markers are of a material that absorbs X-ray from the first X-ray source.

According to an embodiment, the markers are mounted on a frame.

According to an embodiment, the fiducial marker system comprises an array of markers.

According to an embodiment, the X-ray imaging system further comprises a second X-ray source, wherein X-ray from the first X-ray source and X-ray from the second X-ray source are oriented differently relative to the fiducial marker system.

According to an embodiment, the first X-ray source and the second X-ray source are angularly spaced apart.

According to an embodiment, the fiducial marker system comprises four markers; the four markers are coplanar; none of centers of the four markers is collinear with centers of any other two of the four markers; and centers of all the four markers are on vertices of a convex hull of the centers.

Disclosed herein is a method comprising: obtaining an X-ray image using an X-ray imaging system, the X-ray image comprising views of a plurality of markers of a fiducial marker system in the X-ray imaging system and a view of an object in a person being imaged by the X-ray imaging system; identifying the view of the object from the X-ray image; determining a pose of the X-ray imaging system, wherein the image is captured at the pose; and determining a pose of the object based on the pose of the X-ray imaging system, the view of the object, and a 3D model of the object.

According to an embodiment, determining the pose of the object is further based on parameters of or constraints on motion of the object.

According to an embodiment, the parameters of the object comprise geometric parameters of the object, or wherein the parameters of the object comprise a prior pose of the object, or wherein the constraints on the motion of the object are imposed by internal structures of the person.

According to an embodiment, determining the pose of the X-ray imaging system comprises: determining locations and identities of the views of the markers; and determining the pose of the X-ray imaging system based on the locations and identities, parameters of the X-ray imaging system and parameters of the fiducial marker system.

According to an embodiment, determining the locations and identities of the views of the markers comprises: identify areas of the image that represent X-ray intensity below a threshold; determining the identities of the views from the areas using a classifier; and determining the locations of the views based on the identities.

According to an embodiment, the parameters of the X-ray imaging system comprise a prior pose of the X-ray imaging system.

Disclosed herein is a computer program product comprising a non-transitory computer readable medium having instructions recorded thereon, then instructions when executed by a computer implementing any of the above methods.

BRIEF DESCRIPTION OF FIGURES

FIG. 1A schematically shows an X-ray imaging system, according to an embodiment.

FIG. 1B schematically shows a top view of a table and a fiducial marker system of the X-ray imaging system of FIG. 1A, according to an embodiment.

FIG. 2A schematically shows an example of the fiducial marker system.

DETAILED DESCRIPTION

Figure 2B:
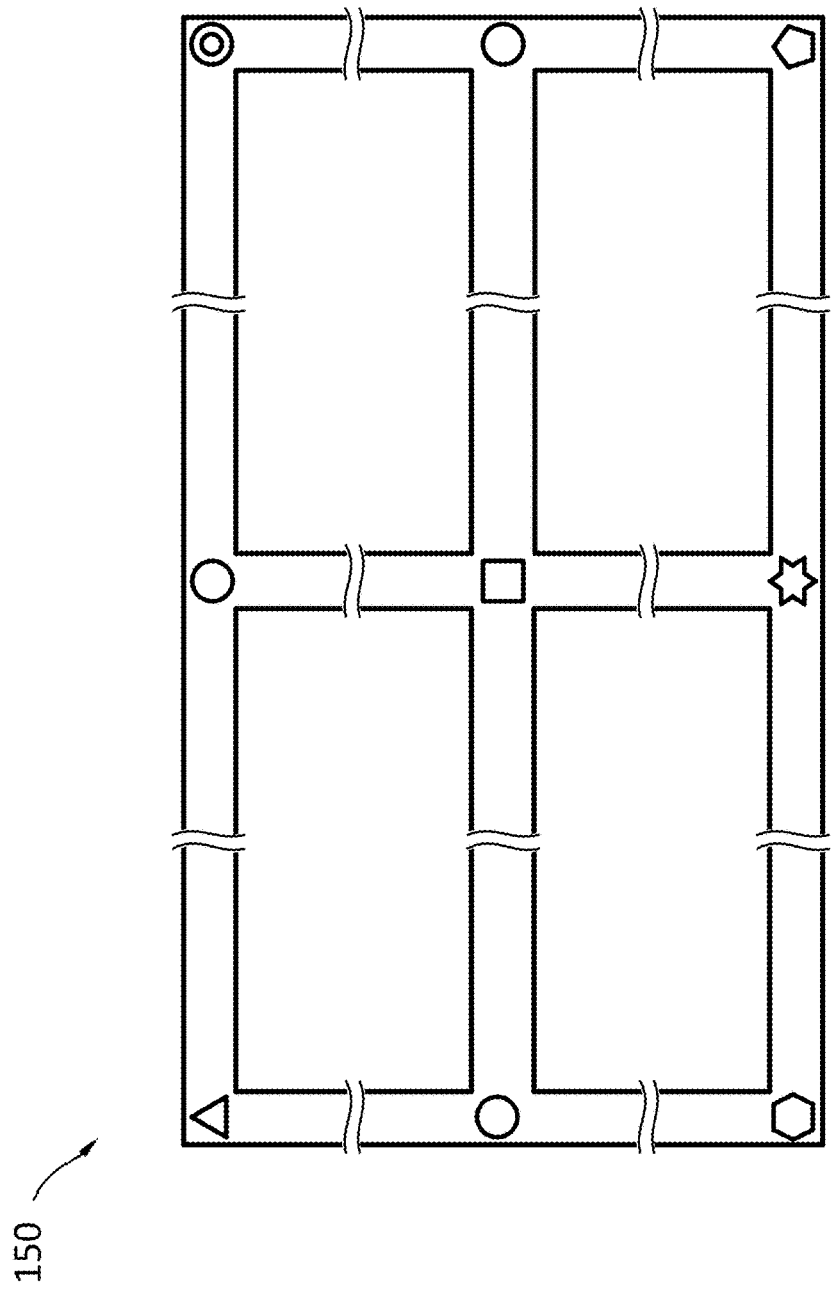
FIG. 2B schematically shows that the fiducial marker system may have an array of markers.

FIG. 1A schematically shows an X-ray imaging system 100 (e.g., a fluoroscopy system), according to an embodiment. The X-ray imaging system 100 comprises an X-ray source 130 and an image sensor 140, spaced apart from each other. The X-ray source 130 and the image sensor 140 may be mechanically connected by a C-arm 110 but other structures are possible.

The X-ray source 130 may be any suitable X-ray source such as an X-ray tube. The X-ray from the X-ray source 130 may be collimated or diverging in one or more directions. The X-ray from the X-ray source 130 may have any wavelength suitable for the particular object imaged.

The image sensor 140 may be any suitable image sensors that can produce real-time images, such as an X-ray image intensifier, a scintillator or a semiconductor X-ray detector.

An X-ray image intensifier includes an input phosphor (e.g., cesium iodide). When X-ray hits the input phosphor, the input phosphor emits visible light. The visible light is directed to a photocathode (e.g., a thin metal layer containing cesium and antimony compounds) and the photocathode emits electrons. The electrons are directed to an output phosphor and the output phosphor produces a visible-light image. The spatial distribution of the brightness of the visible-light image represents the spatial distribution of the X-ray incident on the X-ray image intensifier.

A scintillator (e.g., sodium iodide) absorbs X-ray and emits visible light. A suitable image sensor captures an image of the emitted visible light.

A semiconductor X-ray detector may include a semiconductor layer that absorbs X-ray in wavelengths of interest and generate multiple charge carriers (e.g., electrons and holes). The charge carriers are electronically detected. The amount of charge carriers as a function of location may represent the spatial distribution of the intensity of the X-ray incident on the semiconductor layer.

A table 120 may be configured to be positioned between the X-ray source 130 and the image sensor 140. The X-ray source 130 and the image sensor 140 may move relative to the table 120. For example, the X-ray source 130 and the image sensor 140 may relatively rotate around the table 120 or move sideways or along the table 120. The table 120 is configured to accommodate a person 199 for imaging in the X-ray imaging system 100. For example, the person 199 may lie on the table 120 and undergo a surgery during imaging.

The X-ray imaging system 100 includes a fiducial marker system 150. The fiducial marker system 150 are arranged in such a way that the fiducial marker system 150 does not move relative to the table 120 or the person 199 during imaging. The fiducial marker system 150 may be an integral portion of the table 120 or may be a separate device removably attached to the table 120. The fiducial marker system 150 may be positioned such that at least some part of the fiducial marker system 150 is visible in an image captured by the image sensor 140 during imaging by the X-ray imaging system 100. FIG. 1A shows an example where the X-ray from the X-ray source 130 is projected over the person 199 lying on the table 120 and the fiducial marker system 150 is positioned under the person 199 and within the view of the image sensor 140. FIG. 1B schematically shows a top view of the table 120 and the fiducial marker system 150. The fiducial marker system 150 is positioned under the person 199 and within the imaged area of the person 199.

The fiducial marker system 150 comprises at least three markers that are coplanar. For example, the fiducial marker system 150 may have at least four markers that are coplanar. The centers of the three markers are not collinear. If the fiducial marker system has at least four markers, the centers of all the four markers are on the vertices of the convex hull of the centers of the four markers. Namely, the center of any one of the four markers is outside the triangle formed by the centers of the other three markers. FIG. 2A schematically shows an example of the fiducial marker system 150 including four markers 150A, 150B, 150C and 150D. At least one of the markers is distinct from the other markers. For example, the marker 150A has a unique shape among the four markers; or the marker 150A may have different absorption of the X-ray. The markers 150A and 150C can be distinguished from each other and the markers 150B and 150D in images captured by the image sensor 140. In this particular example, the markers 150A, 150B, 150C and 150D are shown to be a triangle, a circle, a square and a circle, respectively. Many other shapes are possible. The markers of the fiducial marker system 150 may be made of a material that absorbs (e.g., with a mass attenuation coefficient of at least 1000 $cm^2/g$) the X-ray from the X-ray source 130. For example, the markers may contain lead. The markers of the fiducial marker system 150 may be mounted on a frame 159. The frame 159 keeps the relative locations of the markers constant and may not absorb the X-ray as strongly as the markers. Alternatively, the markers may be directly attached to the table 120 without the frame 159. The locations of the markers of the fiducial marker system 150 relative to one another are known. FIG. 2B schematically shows that the fiducial marker system 150 may have an array of markers.

The fiducial marker system 150 provides a visual indication of the pose of the X-ray imaging system 100. The term "pose" of the X-ray imaging system 100 here means the orientation and location of the X-ray source 130 and the image sensor 140 relative to the person 199. In an example, the person 199 does not move relative to the fiducial marker system 150 or the table 120 during imaging, and thus the pose of the X-ray imaging system 100 may be alternatively the orientation and location of the X-ray source 130 and the image sensor 140 relative to the fiducial marker system 150 and the table 120. The pose can be described by 10 parameters: 3 parameters for the location of the X-ray source 130, 2 parameters for the orientation of the X-ray source 130, 3 parameters for the location of the image sensor 140 and 2 parameters for the orientation of the image sensor 140. When the X-ray source 130 and the image sensor 140 have constraints on their locations and orientations, the pose may be described by fewer parameters. For example, in the example shown in FIG. 1A, where the X-ray source 130 and the image sensor 140 are fixed to the C-arm 110, C-arm 110 is constrained to rotate around the table 120 and the table 120 is stationary, the pose of the X-ray imaging system 100 may be described by one parameter (e.g., the angle of rotation of the C-arm 110).

Figure 3:
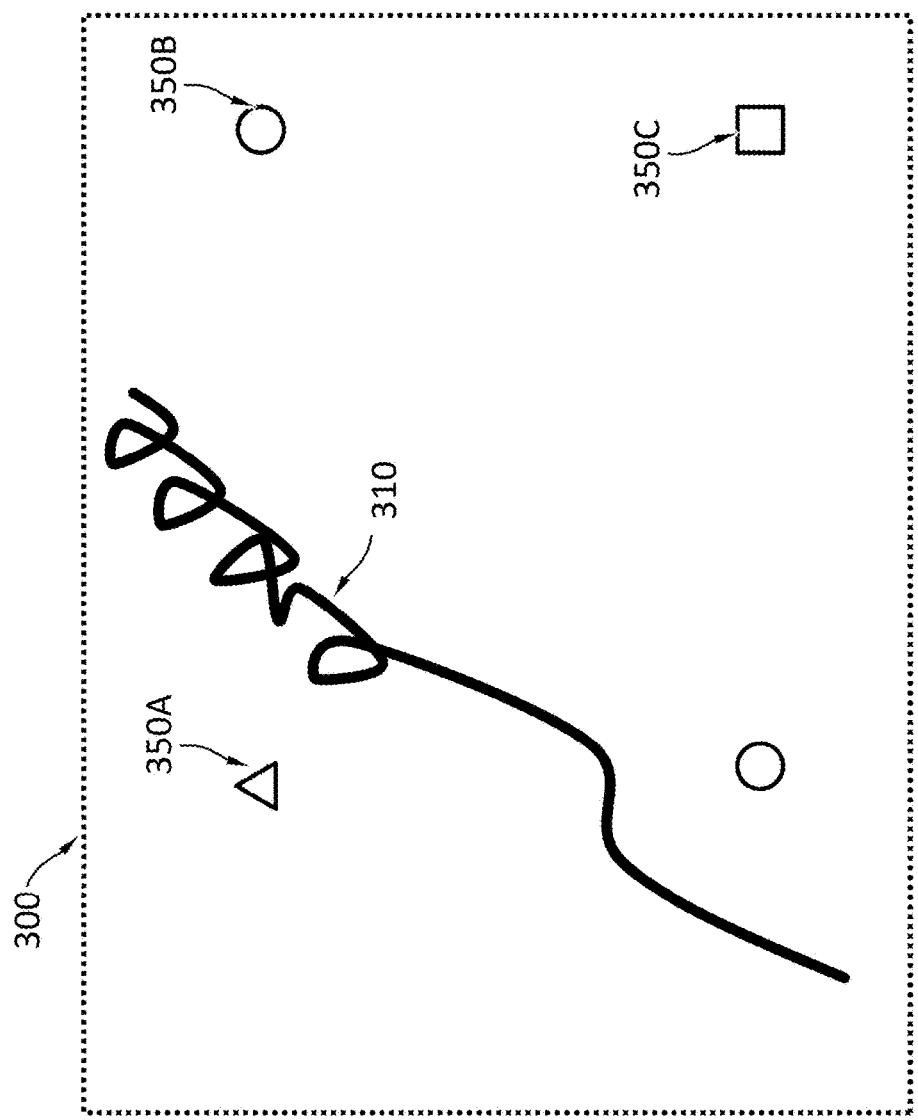
FIG. 3 schematically shows an image captured by an image sensor of the X-ray imaging system.

The pose of the X-ray imaging system 100 may be determined from one or more images captured by the image sensor 140. FIG. 3 schematically shows an image 300 captured by the image sensor 140. The image 300 includes views 350A, 350B and 350C of the markers 150A, 150B and 150C, respectively. The image 300 may further include a view 310 of an object (e.g., a surgical instrument) inside the person 199. The locations and identities of the views 350A, 350B and 350C of the markers 150A, 150B and 150C can be used to determine the pose of the X-ray imaging system 100.

Figure 4:
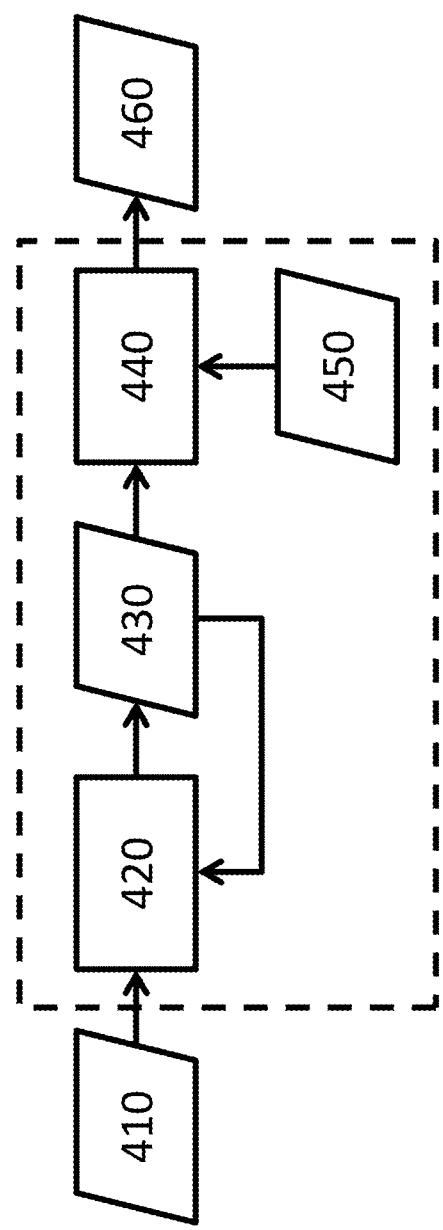
FIG. 4 schematically shows a flow chart for a method of determining the pose of the X-ray imaging system.

FIG. 4 schematically shows a flow chart for a method of determining the pose of the X-ray imaging system 100. In procedure 420, locations and identities 430 of any views of the markers of the fiducial marker system 150 in an X-ray image 410 are determined. The determination of the procedure 420 may take into consideration the prior locations and identities. In procedure 440, the pose 460 of the X-ray imaging system 100 is determined based on the locations and identities 430 and parameters 450 of the X-ray imaging system 100 and the fiducial marker system 150. Examples of the parameters 450 may include the geometric parameters such as the divergence angle of the X-ray, the distance between the X-ray source 130 and the image sensor 140, the distances between the markers, the prior pose of the X-ray imaging system 100, etc. Determination of the pose 460 may be by any suitable method, for example the methods disclosed in Z. Zhang, A flexible new technique for camera calibration, IEEE Transactions on Pattern Analysis and Machine Intelligence, 22(11):1330-1334, 2000, and R. M. Haralick, *Review and Analysis of Solutions of the Three Point Perspective Pose Estimation Problem*, International Journal of Computer Vision, 13(3), 331-356, 1994, the disclosures of which are hereby incorporated by reference in their entirety.

Figure 5:
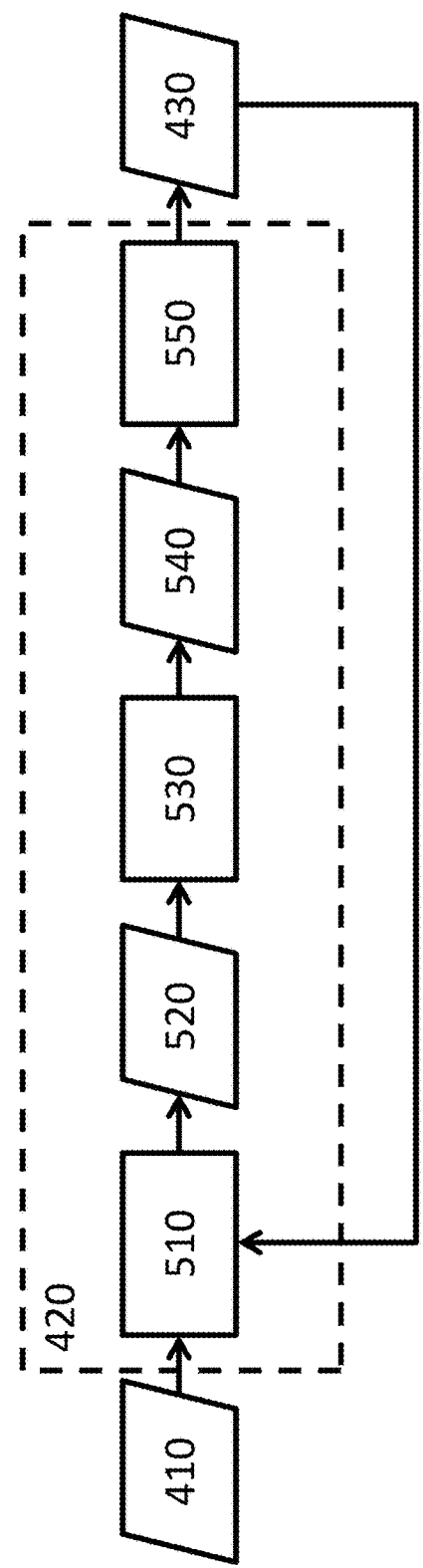
FIG. 5 schematically shows a flow chart for a method of determining locations and identities of views of the markers of the fiducial marker system in an X-ray image.

FIG. 5 schematically shows a flow chart for a method of determining locations and identities 430 of views of the markers of a fiducial marker system in an X-ray image 410. The method represented in FIG. 5 may be used to perform procedure 420 of FIG. 4. In procedure 510, areas 520 of the image 410 that represent X-ray intensity below a threshold are identified. The prior locations and identities may be used in the procedure 510 to identify these areas 520. These areas 520 may contain views of the markers. The areas 520 (or values of their parameters) are fed into a classifier 530 and the classifier 530 determines the identities 540 of the views contained in these areas 520. The locations 550 of the views of the markers are determined based on the identities 540. The locations 550 and the identities 540 constitute the locations and identities 430 of the views.

Figure 6:
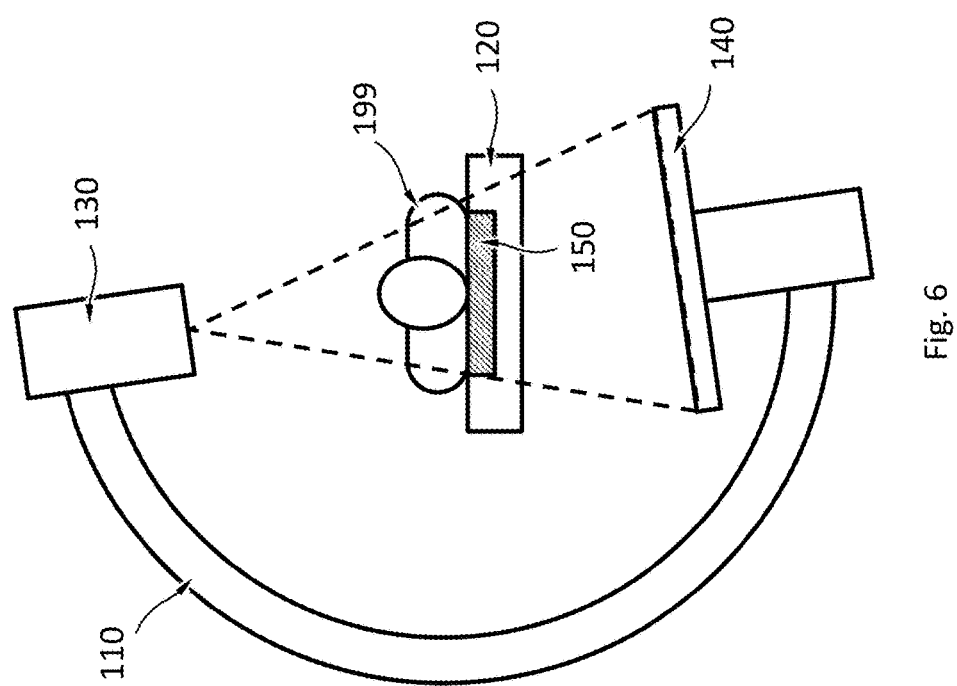
FIG. 6 schematically shows the X-ray imaging system at a different pose from the pose of FIG. 1A.
Figure 7:
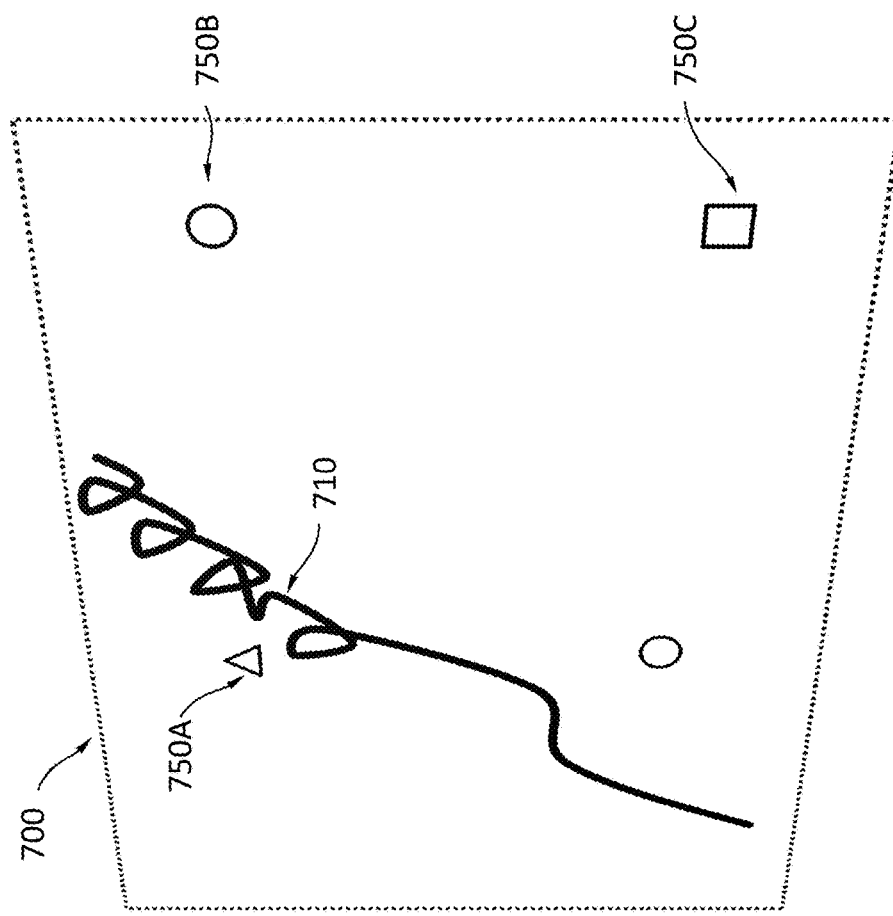
FIG. 7 schematically shows an image captured by an image sensor of the X-ray imaging system at the pose of FIG. 6.

A 3D model of an object inside the person 199 may be constructed from two or more images captured at different poses. For example, in addition to the image 300 of FIG. 3 captured at the pose shown in FIG. 1A, an additional image 700 shown in FIG. 7 may be captured at a different pose shown in FIG. 6. The C-arm 110 of the X-ray imaging system 100 at the pose of FIG. 6 is rotated relative to the table 120 from the pose of FIG. 3. The image 700 includes views 750A, 750B and 750C of the markers 150A, 150B and 150C, respectively. The image 700 may further include a view 710 of an object (e.g., a surgical instrument) inside the person 199. The image 700, including the views 750A, 750B and 750C of the markers 150A, 150B and 150C, and the view 710 of the object, is distorted relative to the image 300, due to the difference in the poses. The 3D model of the object can be constructed from the images 300 and 700.

Figure 8:
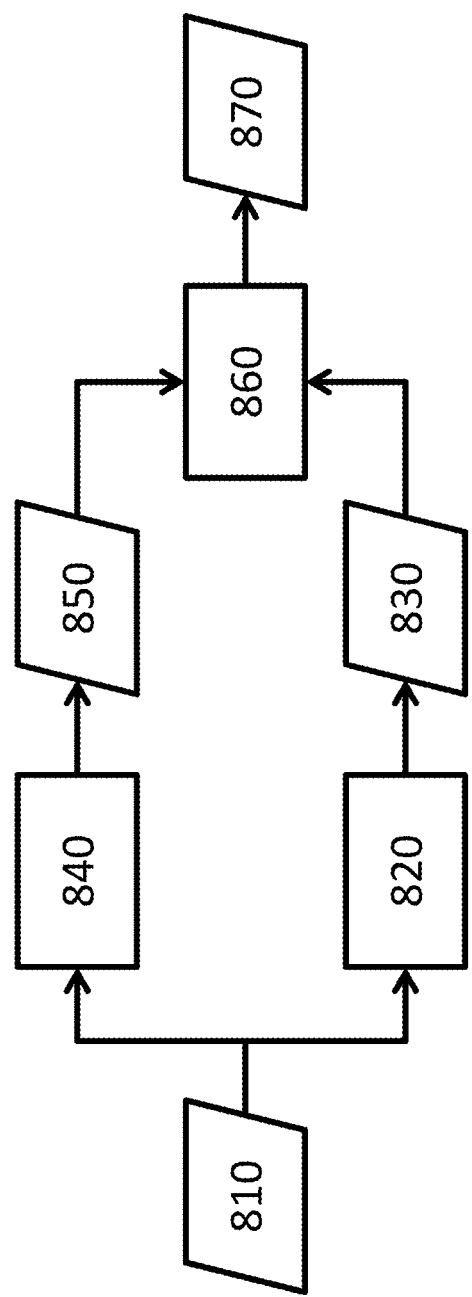
FIG. 8 schematically shows a flow chart for a method of constructing a 3D model of an object in a person being imaged in the X-ray imaging system.

FIG. 8 schematically shows a flow chart for a method of constructing a 3D model of an object. Two or more X-ray images 810 captured at two different poses are obtained. The poses 830 of the X-ray imaging system 100 at which the images 810 are captured are determined (e.g., by using the method presented in FIG. 4) in procedure 820. In procedure 840, the views 850 of the object are identified from the images 810. In procedure 860, the 3D model 870 of the object is determined based on the views 850 and the poses 830.

Figure 9:
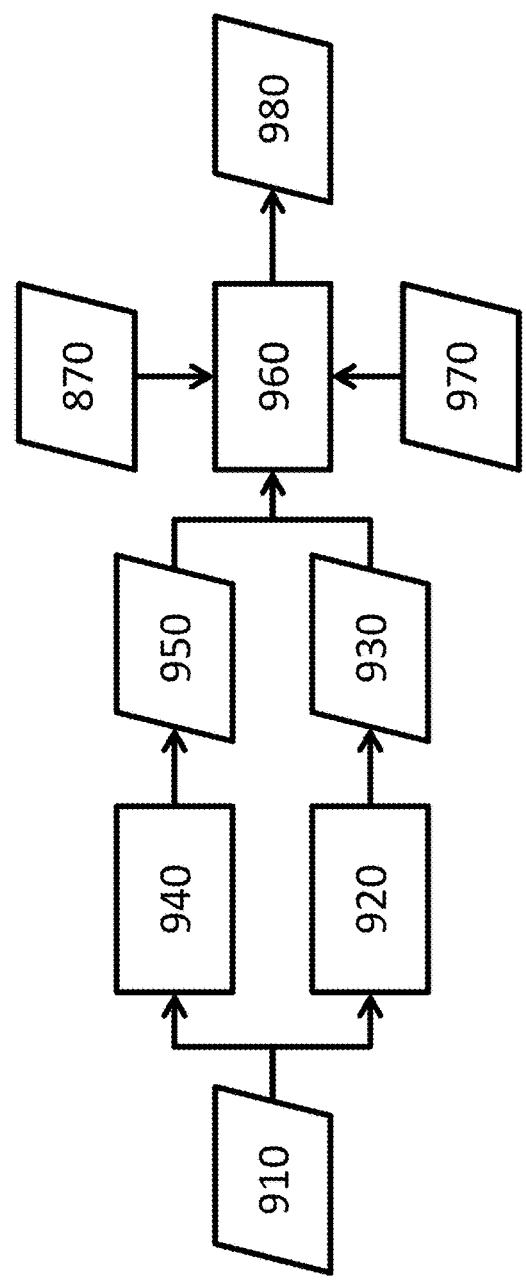
FIG. 9 schematically shows a flow chart for a method of determining the pose of an object in a person being imaged in the X-ray imaging system.

FIG. 9 schematically shows a flow chart for a method of determining the pose of an object in a person 199. The term "pose" of the object here means the orientation and location of the object relative to the person 199. In an example, the person 199 does not move relative to the fiducial marker system 150 or the table 120 during imaging, and thus the pose of the object may be alternatively the orientation and location of the object relative to the fiducial marker system 150 and the table 120. An X-ray image 910 of the person 199 is obtained. The image 910 includes views of the markers of the fiducial marker system 150 and a view of the object. In procedure 940, the view 950 of the object is identified from the image 910. In procedure 920, the pose 930 of the X-ray imaging system 100 at which the image 910 is captured is determined (e.g., by using the method presented in FIG. 4). In procedure 960, the pose 980 of the object is determined based on the pose 930 of the X-ray imaging system 100, the view 950 of the object, the 3D model 870 of the object. Determination of the pose 980 of the object may be further based on parameters of and constraints 970 on the motion of the object. The parameters and constraints 970 may include the geometric parameters (e.g., size, shape) and constraints imposed by the internal structures of the person 199 (e.g., during cardiac catheterization, a catheter can only move along blood vessels). The parameters and constraints 970 may include a prior pose of the object. The method of FIG. 9 may be applied to a series of moving images, thereby tracking 3D movement of the object in real time. The pose of the object may be used to guide movement of the object in the person 199. For example, the pose may be used to guide advancement of a catheter along a blood vessel. The pose of the object may be presented on a monitor or in virtual reality goggles.

The X-ray imaging system 100 may have a processor and a memory. The memory has instructions stored therein. When the processor executes the instructions, the processor may perform the methods of FIG. 4, FIG. 5, FIG. 8 and FIG. 9.

Figure 10:
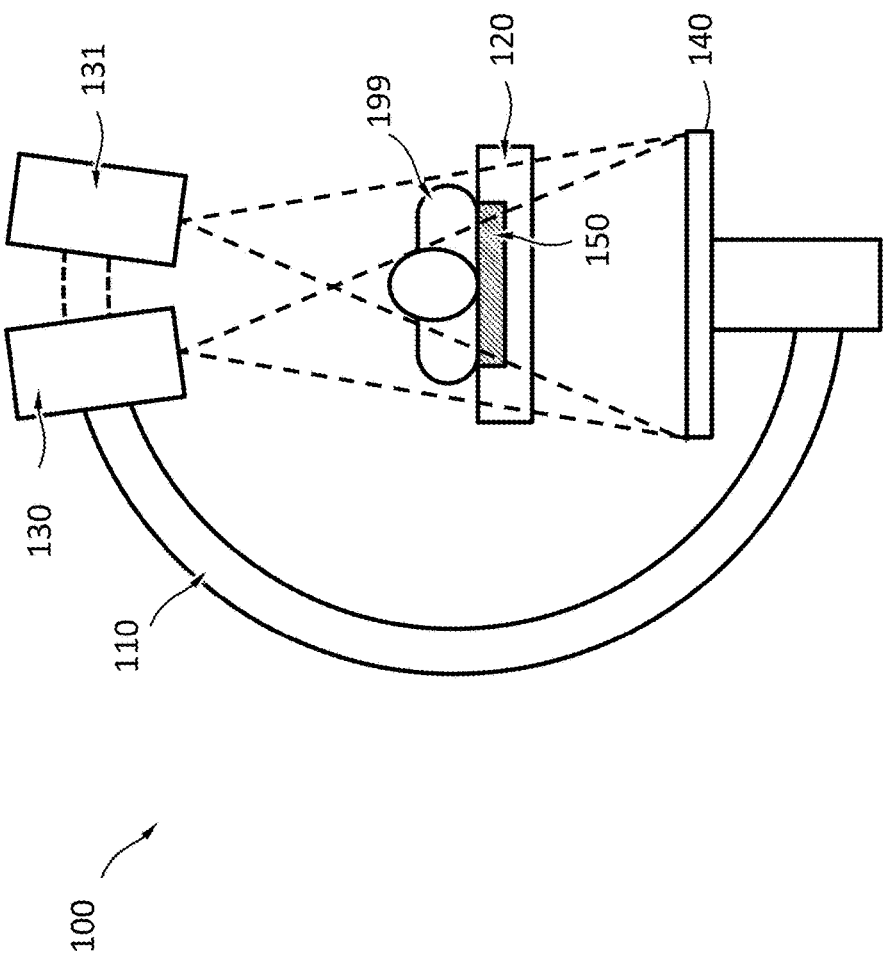
FIG. 10 schematically shows an X-ray imaging system, according to an embodiment.

FIG. 10 schematically shows that the X-ray imaging system 100 may include another X-ray source 131, according to an embodiment. The X-ray from the X-ray source 130 and the X-ray from the second X-ray source 131 are oriented differently relative to the fiducial marker system 150. The X-ray source 130 and the X-ray source 131 may be angularly spaced apart. For example, the X-ray source 130 and the X-ray source 131 may be mounted at different locations on the C-arm 110. The image sensor 140 may capture images using either the X-ray from the X-ray source 130 or the X-ray from the X-ray source 131. The views of the object inside the person 199 are probably different in images captured using the X-ray from the X-ray source 130 and images captured using the X-ray from the X-ray source 131, even without any change of the pose of the X-ray imaging system 100, any movement of the table 120, any movement of the fiducial marker system 150, or any movement of the person 199. One image captured using the X-ray source 130 and one image captured using the X-ray source 131 can be used as the images 810 in the method of FIG. 8 to construct the 3D model 870 of the object, and the 3D model can be used in the flow of FIG. 9 with either image as the image 910 to determine the pose of the object. Either the image captured using the X-ray source 130 or the image captured using the X-ray source 131 may be used as the image 410 in the method of FIG. 4 to determine the pose 460 of the X-ray imaging system 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An X-ray imaging system, comprising:
 a first X-ray source;
 an image sensor, spaced apart from the first X-ray source;
 a table configured to be positioned between the first X-ray source and the image sensor and configured to accommodate a person for imaging in the X-ray imaging system; and
 a fiducial marker system;
 wherein the fiducial marker system comprises three markers, centers of the three markers not being collinear;
 wherein at least one of the three markers is distinct;
 wherein the fiducial marker system comprises four markers;
 wherein the four markers are coplanar;
 wherein none of centers of the four markers is collinear with centers of any other two of the four markers;
 wherein centers of all the four markers are on vertices of a convex hull of the centers.

2. The X-ray imaging system of claim 1, further comprising a C-arm, wherein the first X-ray source and the image sensor are mechanically connected by the C-arm.

3. The X-ray imaging system of claim 1, wherein the first X-ray source and the image sensor are movable relative to the table.

4. The X-ray imaging system of claim 1, wherein the fiducial marker system and the table are connected in such a way that the fiducial marker system does not move relative to the table during imaging.

5. The X-ray imaging system of claim 1, wherein the fiducial marker system is an integral portion of the table.

6. The X-ray imaging system of claim 1, wherein the fiducial marker system is configured to be positioned such that at least some part of the fiducial marker system is visible in an image captured by the image sensor during imaging by the X-ray imaging system.

7. The X-ray imaging system of claim 1, wherein the markers are of a material that absorbs X-ray from the first X-ray source.

8. The X-ray imaging system of claim 1, wherein the markers are mounted on a frame.

9. The X-ray imaging system of claim 1, wherein the fiducial marker system comprises an array of markers.

10. The X-ray imaging system of claim 1, further comprising a second X-ray source, wherein X-ray from the first X-ray source and X-ray from the second X-ray source are oriented differently relative to the fiducial marker system.

11. The X-ray imaging system of claim 10, wherein the first X-ray source and the second X-ray source are angularly spaced apart.

12. A method comprising:
 obtaining an X-ray image using an X-ray imaging system, the X-ray image comprising views of a plurality of markers of a fiducial marker system in the X-ray imaging system and a view of an object in a person being imaged by the X-ray imaging system;
 identifying the view of the object from the X-ray image;
 determining a pose of the X-ray imaging system, wherein the image is captured at the pose; and
 determining a pose of the object based on the pose of the X-ray imaging system, the view of the object, and a 3D model of the object.

13. The method of claim 12, wherein determining the pose of the object is further based on parameters of or constraints on motion of the object.

14. The method of claim 13, wherein the parameters of the object comprise geometric parameters of the object, or wherein the parameters of the object comprise a prior pose of the object, or wherein the constraints on the motion of the object are imposed by internal structures of the person.

15. The method of claim 12, wherein determining the pose of the X-ray imaging system comprises:
 determining locations and identities of the views of the markers; and
 determining the pose of the X-ray imaging system based on the locations and identities, parameters of the X-ray imaging system and parameters of the fiducial marker system.

16. The method of claim 15, wherein determining the locations and identities of the views of the markers comprises:
 identify areas of the image that represent X-ray intensity below a threshold;
 determining the identities of the views from the areas using a classifier; and
 determining the locations of the views based on the identities.

17. The method of claim 15, wherein the parameters of the X-ray imaging system comprise a prior pose of the X-ray imaging system.

18. A computer program product comprising a non-transitory computer readable medium having instructions recorded thereon, then instructions when executed by a computer implementing the method of claim 12.

\* \* \* \* \*